United States Patent
Lee et al.

(10) Patent No.: US 11,066,687 B2
(45) Date of Patent: Jul. 20, 2021

(54) 5'-INOSINIC ACID DEHYDROGENASE AND METHOD OF PREPARING 5'-INOSINIC ACID USING THE SAME

(71) Applicant: CJ CHEILJEDANG CORPORATION, Seoul (KR)

(72) Inventors: Ji Hye Lee, Anyang-si (KR); So-jung Park, Suwon-si (KR); Min Ji Baek, Suwon-si (KR); Jin Sook Chang, Suwon-si (KR); Byoung Hoon Yoon, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/482,608

(22) PCT Filed: Aug. 16, 2018

(86) PCT No.: PCT/KR2018/009378
§ 371 (c)(1),
(2) Date: Jul. 31, 2019

(87) PCT Pub. No.: WO2020/022547
PCT Pub. Date: Jan. 30, 2020

(65) Prior Publication Data
US 2021/0139939 A1    May 13, 2021

(51) Int. Cl.
| | |
|---|---|
| C12P 19/40 | (2006.01) |
| C12P 9/00 | (2006.01) |
| C12P 19/32 | (2006.01) |
| C12N 9/00 | (2006.01) |
| C12N 15/77 | (2006.01) |
| C12N 9/04 | (2006.01) |

(52) U.S. Cl.
CPC ............ *C12P 19/40* (2013.01); *C12N 9/0006* (2013.01); *C12N 15/77* (2013.01); *C12P 19/32* (2013.01); *C12Y 101/01205* (2013.01)

(58) Field of Classification Search
CPC ........ C12P 19/40; C12P 19/32; C12N 9/0006; C12N 15/77; C12Y 101/01205
See application file for complete search history.

(56) References Cited

U.S. PATENT DOCUMENTS 8,309,329 B2 *  11/2012  Asahara ............... C12N 9/0006
                                                                435/87

FOREIGN PATENT DOCUMENTS

| KR | 2002-0053892 A | 7/2002 |
| KR | 2002-0074811 A | 10/2002 |
| KR | 2010-0127784 A | 12/2010 |
| KR | 2016-0059960 A | 5/2016 |
| KR | 2016-0078694 A | 7/2016 |

OTHER PUBLICATIONS

Asahara et al., "Accumulation of gene-targeted Bacillus subtilis mutations that enhance fermentative inosine production," *Appl Microbiol Biotechnol* 87:2195-2207, 2010.
Genbank, "IMP dehydrogenase," Acc No. ART22012, pp. 1-2, 2017.
Genbank, "FASTA Graphics," Acc No. CP014634, pp. 1-802, 2016.
Peifer et al., "Metabolic engineering of the purine biosynthetic pathway in *Corynebacterium glutamicum* results in increased intracellular pool sizes of IMP and hypoxanthine," *Microbial Cell Factories* 11(138):1-14, 2012.
Futer et al., "A mutational analysis of the active site of human type II inosine 5'-monophosphate dehydrogenase," *Biochimica et Biophysica Acta* 1594:27-39 (2002).
NCBI Reference Sequence: WP 066792489.1, IMP dehydrogenase [*Corynebacterium stationis*] (1 page) (Aug. 18, 2016).
Ledesma-Amaro et al., "Increased production of inosine and guanosine by means of metabolic engineering of the purine pathway in *Ashbya gossypii*," *Microbial Cell Factories* 14:58 (8 pages) (2015).
Wang et al., "Mutagenetic study of a novel inosine monophosphate dehydrogenase from *Bacillus amyloliquefaciens* and its possible application in guanosine production," *Biotechnology & Biotechnological Equipment* 28(1):102-106 (2014).
Matsui et al., "gsk Disruption Leads to Guanosine Accumulation in *Escherichia coli*," *Biosci. Biotechnol. Biochem.* 65(5):1230-1235 (2001).

* cited by examiner

*Primary Examiner* — Robert J Yamasaki
*Assistant Examiner* — Charles Zoltan Constantine
(74) *Attorney, Agent, or Firm* — Seed IP Law Group LLP

(57) ABSTRACT

Provided are a variant of 5'-inosinic acid dehydrogenase, a microorganism including the same, and a method of preparing 5'-inosinic acid using the same.

15 Claims, No Drawings

Specification includes a Sequence Listing.

US 11,066,687 B2

5'-INOSINIC ACID DEHYDROGENASE AND METHOD OF PREPARING 5'-INOSINIC ACID USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_447USPC_SEQUENCE_LISTING.txt. The text file is 27.4 KB, was created on Jun. 10, 2019, and is being submitted electronically via EFS-Web.

BACKGROUND OF THE INVENTION

1. Field of the Invention

The present disclosure relates to a variant of 5'-inosinic acid dehydrogenase, a microorganism including the same, and a method of preparing 5'-inosinic acid using the same.

2. Description of the Related Art

5'-Inosinic acid (5'-inosine monophosphate, hereinafter referred to as IMP), which is a nucleotide-based material, is an intermediate material of the metabolic system of nucleic acid biosynthesis, and is used in a variety of fields, such as medical products and medical applications. IMP is a material that is widely used as a food seasoning additive or used for foods, together with 5'-guanylic acid (5'-guanine monophosphate, hereinafter referred to as GMP). IMP itself is known to have a beef flavor, and is known to enhance the flavor of monosodium glutamic acid (hereinafter referred to as MSG), like GMP. Therefore, IMP has received much attention as a nucleotide-based taste seasoning.

Methods of preparing IMP include a method of enzymatically degrading ribonucleic acids which are extracted from yeast cells, a method of chemically phosphorylating inosine which is produced by fermentation (Agri. Biol. Chem., 36, 1511(1972), etc.), a method of culturing a microorganism capable of directly producing IMP and then recovering IMP in a culture thereof, etc. Among these, the most commonly used method is that of using the microorganism capable of directly producing IMP.

Meanwhile, enzymes in their natural state do not always exhibit optimal properties in terms of activity, stability, substrate specificity for optical isomers, etc., which are required in industrial applications. Therefore, various attempts have been made to improve enzymes through mutations of their amino acid sequences, etc., such that they become suitable for the intended use. Of these, rational design and site-directed mutagenesis of enzymes have been applied in order to improve enzyme functions. However, in many cases, there is a disadvantage in that information on the structure of a target enzyme is not sufficient or a structure-function relationship is not clear, and therefore, the methods cannot be effectively applied. In this regard, it has been reported that attempts at enzyme improvement have been made by a directed evolution method of screening for an enzyme of a desired trait from a mutant enzyme library which is constructed through random mutagenesis of the enzyme gene, leading to improvement of its activity.

The present inventors have conducted extensive studies to produce IMP in a high yield by the method of directly producing IMP through microbial fermentation, and they have identified a variant of a protein involved in IMP productivity, thereby completing the present disclosure.

SUMMARY OF THE INVENTION

An object of the present disclosure is to provide a variant of 5'-inosinic acid dehydrogenase.

Another object of the present disclosure is to provide a polynucleotide encoding the variant of 5'-inosinic acid dehydrogenase.

Still another object of the present disclosure is to provide a vector including the polynucleotide.

Still another object of the present disclosure is to provide a microorganism producing 5'-inosinic acid, including the variant of 5'-inosinic acid dehydrogenase and the vector.

Still another object of the present disclosure is to provide a method of preparing 5'-inosinic acid, the method including the steps of culturing a microorganism of the genus *Corynebacterium* in a medium; and recovering 5'-inosinic acid from the microorganism or the medium.

DETAILED DESCRIPTION OF THE PREFERRED EMBODIMENTS

The preferred embodiments are described in detail is as follows. Meanwhile, respective descriptions and embodiments disclosed in this application may also be applied to other descriptions and embodiments. That is, all combinations of various elements disclosed in this application fail within the scope of the present application. Further, the scope of the present application is not limited by the specific description below.

In order to achieve the above objects, an aspect of the present disclosure provides a variant oi 5'-inosinic acid dehydrogenase having a polypeptide including substitution of one or more amino acids in an amino acid sequence of SEQ ID NO: 2. Specifically, the present disclosure provides the variant of 5'-inosinic acid dehydrogenase having the polypeptide including substitution of one or more amino acids in the amino acid sequence of SEQ ID NO: 2, wherein the amino acid substitution includes at least any one selected from the group consisting of substitution of an amino acid at position 377 with threonine and substitution of an amino acid at position 499 from the N-terminus with isoleucine. Another aspect of the present disclosure provides a variant of 5'-inosinic acid dehydrogenase having 5'-inosinic acid dehydrogenase activity, the variant having an amino acid sequence including substitution of the amino acid at position 377 with threonine, substitution of the amino acid at position 499 with isoleucine in the amino acid sequence of SEQ ID NO: 2, or a combination thereof. Specifically, the variant of 5'-inosinic acid dehydrogenase may include substitution of one or more amino acids in the amino acid sequence of SEQ ID NO: 2, wherein the amino acid substitution may include at least any one selected from the group consisting of substitution of the amino acid at position 377 with threonine and substitution of the amino acid at position 499 with isoleucine.

As used herein, the term "5'-inosinic acid dehydrogenase" refers to a protein involved in the production of 5'-inosinic acid (5'-inosine monophosphate; IMP). With respect to the objects of the present disclosure, the term may be used interchangeably with inosine-5'-monophosphate dehydrogenase, IMP dehydrogenase, inosinic acid dehydrogenase, IMPDH, etc.

In the present disclosure, SEQ ID NO: 2 refers to an amino acid sequence having 5'-inosinic acid dehydrogenase activity. Specifically, SEQ ID NO: 2 is a sequence of a protein having 5'-inosinic acid dehydrogenase activity, which is encoded by guaB gene. The amino acid sequence of SEQ ID NO: 2 may be obtained from NCBI GenBank, which is a public database. For example, the amino acid sequence or SEQ ID NO: 2 may be derived from *Corynebacterium stationis*, but is not limited thereto, and may include any sequence having the same activity as that of the above amino acid sequence without limitation. Further, the amino acid sequence may include the amino acid sequence of SEQ ID NO: 2 or an amino acid sequence having 80% or more homology or identity to the amino acid sequence of SEQ ID NO: 2, but is not limited thereto. Specifically, the amino acid sequence may include the amino acid sequence of SEQ ID NO: 2 or an amino acid sequence having at least 80%, 85%, 90%, 95%, 96, 97%, 98%, or 99 or more homology or identity to the amino acid sequence of SEQ ID NO: 2. The amino acid sequence having homology or identity may be those from the above range, excluding a sequence having 100% identity, or may be a sequence having less than 100% identity. Further, it is apparent that a protein having an amino acid sequence having deletion, modification, substitution, or addition of some amino acids also falls within the scope of the present invention as long as it has the homology or identity and exhibits efficacy corresponding to that of the above protein.

As used herein, the term "variant or 5'-inosinic acid dehydrogenase" may be used interchangeably with a variant polypeptide having abilities to produce IMP, an IMP-producing variant polypeptide, a variant polypeptide having 5'-inosinic acid productivity, a 5'-inosinic acid-producing variant polypeptide, a variant polypeptide having 5'-inosinic acid dehydrogenase activity, a 5'-inosinic acid dehydrogenase variant, etc. Further, the protein may be derived from the genus *Corynebacterium*, specifically, *Corynebacterium stationis*, but is not limited thereto.

The variant of 5'-inosinic acid dehydrogenase may include variation at position 377 and/or at position 499 from the N-terminus in the amino acid sequence of SEQ ID NO: 2. The variant of 5'-inosinic acid dehydrogenase may be one having substitution of the amino acid at position 377 with another amino acid, substitution of the amino acid at position 499 with another amino acid, or substitution of the amino acid at position 377 with smother amino acid and substitution of the amino acid at position 499 with another amino acid, and having weakened activity, as compared with those including the amino acid sequence of SEQ ID NO: 2 or a non-modified 5'-inosinic acid dehydrogenase derived from the wild-type microorganism. Such a variant of 5'-inosinic acid dehydrogenase means those having variation of the amino acid(s) at position 377 and/or at position 499 from N-terminus in SEQ ID NO: 2 and/or in an amino acid sequence having at least 80%, 85%, 90%, 95%, 96%, 97%, 98%, or 99% or more homology or identity to SEQ ID NO: 2, as described above.

Specifically, the variant of 5'-inosinic acid dehydrogenase may have substitution of the amino acid at position 377 with threonine, substitution of the amino acid at position 499 with isoleucine, or substitution of the amino acid at position 377 with threonine and substitution of the amino acid at position 499 with isoleucine in the amino acid sequence of SEQ ID NO: 2, and the polypeptide may have weakened 5'-inosinic acid dehydrogenase activity, as compared with the polypeptide including the amino acid sequence of SEQ ID NO: 2, but is not limited thereto.

With respect to the objects of the present disclosure, the microorganism including the variant of 5'-inosinic acid dehydrogenase is characterized in that amount of IMP produced is increased. This is significant in that amount of IMP produced may be increased by the variant of 5'-inosinic acid dehydrogenase of the present disclosure, whereas a wild-type strain of the genus *Corynebacterium* is not able to produce IMP or, even if it can produce IMP, it is only able to produce a very small amount thereof.

Specifically, the variant of 5'-inosinic acid dehydrogenase including the amino acid sequence having substitution of the amino acid at position 377 with another amino acid, substitution or the amino acid at position 499 with another amino acid, or substitution of the amino acid at position 377 with another amino acid and substitution of the amino acid at position 499 with another amino acid in the amino acid sequence represented by SEQ ID NO: 2 may include at least any one selected from the group consisting of SEQ ID NOS: 6, 7, and 8. More specifically, the variant of 5'-inosinic acid dehydrogenase having substitution of the amino acid at position 377 with threonine, substitution of the amino acid at position 499 with isoleucine, or substitution of the amino acid at position 377 with threonine and substitution of the amino acid at position 499 with isoleucine in the amino acid sequence of SEQ ID NO: 2 may include at least any one selected from the group consisting of SEQ ID NOS: 6, 7, and 8. The variant of 5'-inosinic acid dehydrogenase may consist of at least any one selected from the group consisting of SEQ ID NOS: 6, 7, and 8. Further, the variant of 5'-inosinic acid dehydrogenase may include the amino acid sequence having SEQ ID NO: 6, 7, or 8 or an amino acid sequence having 80% or more homology or identity thereto, but is not limited thereto. Specifically, the variant of 5'-inosinic acid dehydrogenase of the present disclosure may include a polypeptide having SEQ ID NO: 6, 7, or 8 and a polypeptide having at least 80%, 85%, 90%, 95%, 96%, 97%, 98%, or 99% or more homology or identity to SEQ ID NO: 6, 7, or 8. Further, it is apparent that a protein having an amino acid sequence having deletion, modification, substitution, or addition of some amino acids, in addition to the amino acid at position 377 or 499, also falls within the scope of the present invention as long as it has the homology or identity and exhibits efficacy corresponding to that of the above protein.

In other words, even though the present disclosure describes a 'protein or polypeptide having an amino acid sequence represented by a particular SEQ ID NO', it is apparent that a protein having an amino acid sequence having deletion, alteration, substitution, conservative substitution, or addition of some amino acids may also be used in the present disclosure, as long as it has activity identical or corresponding to that of the polypeptide having the amino acid sequence of the corresponding SEQ ID NO. For example, as long as a protein has the activity identical or corresponding to that of the variant of 5'-inosinic acid dehydrogenase, it does not exclude addition of sequences which does not alter function of the protein at the front of and the end of the amino acid sequence, naturally occurring mutation, silent mutation, or conservative substitution thereof. It is apparent that a protein having such a sequence addition or mutation also fails within the scope or the present disclosure.

The "conservative substitution" means replacement of an amino acid with another amino acid having similar structural and/or chemical properties. This amino acid substitution may be generally made on the basis of similarity in polarity, charge, solubility, hydrophobicity, hydrophilicity, and/or amphipathic nature. For example, positively charged (basic) amino acids include arginine, lysine, and histidine; and negatively charged (acidic) amino acids include glutamic acid and aspartic acid; aromatic amino acids include phenylalanine, tryptophan, and tyrosine; and hydrophobic amino acids include alanine, valine, isoleucine, leucine, methionine, phenylalanine, tyrosine, and tryptophan.

Therefore, in the present disclosure, the "variant" may further include conservative substitution and/or modification of one or more amino acids in 'a protein or polypeptide having an amino acid sequence represented by a particular SEQ ID NO'. For example, certain variants may include variants in which one or more portions, such as a N-terminal leader sequence or transmembrane domain, have been removed. Other variants may include variants in which a portion has been removed from the N- and/or C-terminus or the mature protein. The variant may also include other modifications, including deletion or addition of amino acids, which have minimal effects on properties and a secondary structure of the polypeptide. For example, the polypeptide may be conjugated to a signal (or leader) sequence at the N-terminal end of a protein that co-translationally or post-translationally directs transfer of the protein. The polypeptide may also be conjugated to another sequence or a linker for ease of identification, purification, synthesis of the polypeptide. The term "variant" may be used interchangeably with modification, modified protein, modified polypeptide, mutant, mutein, divergent, etc., and any term may be used without limitation, as long as it is used in a sense of being modified.

Homology and identity mean a degree of relatedness between two given amino acid sequences or nucleotide sequences, and may be expressed as a percentage.

The terms "homology and identity" may often be used interchangeably with each other.

Sequence homology or identity of a conserved polynucleotide or polypeptide may be determined by a standard alignment algorithm used with default gap penalties established by a program to be used. Substantially, homologous or identical sequences may hybridize under moderately or highly stringent conditions along their entire sequence or at least about 50', about 60%, about 70%, about 80, or about 90% of the entire length. With regard to the polynucleotides to be hybridized, polynucleotides including a degenerate codon instead of a codon may also be contemplated.

Whether any two polynucleotide or polypeptide sequences have homology, similarity, or identity may be determined by, for example, a known computer algorithm such as the "FASTA" program using default parameters as in Pearson et al. (1983)[Proc. Natl. Acad. Sci. USA 85]: 2444, and alternatively, may be determined by using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277) (version 5.0.0 or later) (including GCG program package (Devereux, J., et al., Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1983) SIAM J Applied Math 48: 1073). For example, homology, similarity, or identity may be determined using BLAST, or ClustalW of the National Center for Biotechnology information.

Homology, similarity, or identity of polynucleotides or polypeptides may be determined by comparing sequence information using a GAP computer program such as Needleman et al. (1970), J Mol Biol. 48: 443, as disclosed in Smith and Waterman, Adv. Appl. Math (1981) 2:482. Briefly, the GAP program defines similarity as the number of aligned symbols (i.e., nucleotides or amino acids) which are similar, divided by the total number of symbols in the shorter of the two sequences. The default parameters for the GAP program may include: (1) a unary comparison matrix (containing a value of 1 for identities and 0 for non-identities) and the weighted comparison matrix (or EDNAFILL (EMBOSS version of NCBI NUC4.4) substitution matrix) of Gribskov et al. (1986) Nucl. Acids Res. 14: 6745, as described by Schwartz and Dayhoff, eds., Atlas Of Protein Sequence And Structure, National Biomedical Research Foundation, pp. 353-353 (1979); (2) a penalty or 3.0 for each gap and an additional 0.10 penalty for each symbol in each gap (or gap open penalty 10, gap extension penalty 0.5); and (3) no penalty for end gaps. Therefore, the term "homology" or "identity", as used herein, represents relevance between sequences.

It is apparent that a polynucleotide to be translated, due to codon degeneracy, into a polypeptide having an amino acid sequence selected from the group consisting of SEQ ID NOS: 6, 7, and 8, or a polypeptide having homology or identity thereto may also be included. For example, the polynucleotide may have a nucleotide sequence selected from the group consisting of SEQ ID NOS: 3, 4, and 5. Further, by hybridization under stringent conditions with a probe prepared from a known gene sequence, for example, a sequence complementary to all or a part of the nucleotide sequence, a polynucleotide sequence encoding a variant of 5'-inosinic acid dehydrogenase, which includes an amino acid sequence having substitution of the amino acid at position 377 with threonine, or substitution of the amino acid at position 499 with isoleucine in the amino acid sequence of SEQ ID NO: 2 may be included without limitation.

Still another aspect of the present disclosure provides a polynucleotide encoding the variant of 5'-inosinic acid dehydrogenase or a vector including the polynucleotide.

As used herein, the term "polynucleotide" refers to a DNA or RNA strand having more than a certain length as a nucleotide polymer which is a long chain of nucleotide monomers connected by a covalent bond, and more specifically, to a polynucleotide fragment encoding the polypeptide.

The polynucleotide encoding the variant of 5'-inosinic acid dehydrogenase of the present disclosure may include any polynucleotide sequence without limitation, as long as it encodes the variant polypeptide having 5'-inosinic acid dehydrogenase activity of the present disclosure. In the present disclosure, a gene encoding the amino acid sequence of 5'-inosinic acid dehydrogenase is guaB gene, and specifically, the gene may be derived from *Corynebacterium stationis*, but is not limited thereto.

Specifically, due to codon degeneracy or by considering codons preferred by a microorganism in which the polypeptide is able to be expressed, various modifications may be made in the coding region of the polynucleotide of the present disclosure within the scope that does not change the amino acid sequence of the polypeptide. Any polynucleotide sequence may be included without limitation as long as it encodes the variant of 5'-inosinic acid dehydrogenase having substitution of the amino acid at position 377 with another amino acid, substitution of the amino acid at position 499 with another amino acid, or substitution of the amino acid at position 377 with another amino acid and substitution of the amino acid at position 499 with another amino acid in the amino acid sequence of SEQ ID NO: 2.

For example, the polynucleotide encoding the variant of 5'-inosinic acid dehydrogenase of the present disclosure may have a polynucleotide sequence encoding an amino acid sequence selected from the group consisting of SEQ ID NOS: 6, 7, and 8, but is not limited thereto. More specifically, the polynucleotide may have a polynucleotide sequence selected from the group consisting of SEQ ID NOS: 3, 4, and 5, but is not limited thereto.

Further, by hybridization under stringent conditions with a probe prepared from a known gene sequence, for example, a sequence complementary to all or a part of the nucleotide sequence, a sequence encoding a protein having activity of the variant of 5'-inosinic acid dehydrogenase having substitution of the amino acid at position 377 with another amino acid, substitution of the amino acid at position 499 with another amino acid, or substitution of the amino acid at position 377 with another amino acid and substitution of the amino acid at position 499 with another amino acid in the amino acid sequence of SEQ ID NO: 2 may be included without limitation. The "stringent conditions" mean conditions that permit hybridization between polynucleotides. Such conditions are described in detail in the literature (e.g., J. Sambrook et al., the same as above).

The stringent conditions may include conditions under which genes having high homology or identity, for instance, genes having 40% or more, specifically 90% or more, more specifically 95% or more, still more specifically 97% or more, particularly specifically 99% or more homology or identity are able to hybridize to each other, conditions under which genes having lower homology or identity are not able to hybridize to each other, or conditions which are common washing conditions for Southern hybridization, e.g., a salt concentration and a temperature corresponding to 60° C., IX SSC, 0.1 SDS, specifically 60° C., 0.1×SSC, 0.1% SDS, more specifically 6° C., 0.1×SSC, 0.11 SDS, once, specifically, twice or three times.

Hybridization requires that two nucleic acids have complementary sequences, although mismatches between bases are possible depending on stringency of hybridization. The term "complementary" is used to describe the relationship between nucleotide bases that are able to hybridize to one another. For example, with respect to DNA, adenosine is complementary to thymine and cytosine is complementary to guanine. Accordingly, the present disclosure may also include isolated nucleic acid fragments complementary to the complete sequences as well as substantially similar nucleic acid sequences.

Specifically, a polynucleotide having homology or identity may be detected by hybridization conditions including a hybridization step at T. of 55° C. and by utilizing the above-described conditions. Further, the $T_m$ value may be 60° C., 63° C., or 65° C., but is not limited thereto, and properly controlled by those skilled in the art according to the purpose.

The appropriate stringency for hybridizing polynucleotides depends on the length of the polynucleotides and the degree of complementation, and variables are well known in the art (see Sambrook et al., supra, 9.50-9.51, 11.7-11.8).

In the present disclosure, the gene encoding the amino acid sequence or the variant of 5'-inosinic acid dehydrogenase is guaB gene, and a polynucleotide encoding the same is the same as described above.

In the present disclosure, the polynucleotide encoding the variant of 5'-inosinic acid dehydrogenase is also the sane as described above.

As used herein, the term "vector" means a DNA construct containing the nucleotide sequence of the polynucleotide encoding the desired polypeptide which is operably linked to a suitable regulatory sequence such that the desired polypeptide is expressed in a suitable host. The regulatory sequences may include a promoter to direct transcription, a certain operator sequence to regulate such transcription, a sequence encoding a suitable ribosome-binding site on mRNA, and a sequence to regulate termination of transcription and translation. Once transformed into a suitable host, the vector may replicate or function independently of the host genome, or may integrate into the genome itself.

The vector used in the present disclosure may not be particularly limited as lore as the vector is replicable in the host cell, and any vector known in the art may be used. Examples of the vector commonly used may include natural or recombinant plasmids, cosmids, viruses, and bacteriophages. For example, as a phage vector or a cosmid vector, pWE15, M13, MBL3, MBL4, IXII, ASHII, APII, t10, t11, Charon4A, Charon21A, etc. may be used, and as a plasmid vector, those based on pBP, pUC, pBluescriptII, pGEM, pTZ, pCL, pET, etc. may be used. Specifically, pDZ, pACYC177, pACYC184, pCL, pECCG117, pUC19, pBR322, pMW18, pCC1BAC vector, etc. may be used.

For example, the polynucleotide encoding the desired polypeptide may be inserted into the chromosome. The insertion of the polynucleotide into the chromosome may be performed using any method known in the art, e.g., by homologous recombination, but is not limited thereto. A selection marker for confirming the insertion of the vector into the chromosome may be further included. The selection marker is used for selection of cells transformed with the vector, i.e., in order to confirm whether the desired nucleic acid molecule has been inserted, and markers capable of providing selectable phenotypes such as drug resistance, auxotrophy, resistance to cytotoxic agents, and expression of surface polypeptides may be used. Under the circumstances where selective agents are treated, only the cells capable of expressing the selection markers can survive or express other phenotypic traits, and thus the transformed cells may be easily selected. In still another aspect of the present disclosure, the present disclosure provides a microorganism producing 5'-inosinic acid by including the variant of 5'-inosinic acid dehydrogenase or the polynucleotide encoding the same. Specifically, the microorganism including the variant of 5'-inosinic acid dehydrogenase and/or the polynucleotide encoding the same may be a microorganism prepared by transformation with a vector including the polynucleotide, but is not limited thereto.

As used herein, the term "transformation" refers to a process of introducing a vector which includes a polynucleotide encoding a target protein into a host cell such that the protein encoded by the polynucleotide is able to be expressed in the host cell. It does not matter whether the transformed polynucleotide is inserted into the chromosome of a host cell and located thereon or located outside of the chromosome, as long as the transformed polynucleotide may be expressed in the host cell. Further, the polynucleotide may include DNA and RNA encoding the target protein. The polynucleotide may be introduced in any form, as long as the polynucleotide may be introduced into the host cell and expressed therein. For example, the polynucleotide may be introduced into the host cell in the form of an expression cassette, which is a gene construct including all elements required for its autonomous expression. The expression cassette may include a promoter, a transcription termination signal, a ribosome binding site, and a translation termination signal that may be operably linked to the polynucleotide. The expression cassette may be in a form or an expression vector performing self-replication. In addition, the polynucleotide may be introduced into the host cell as is to be operably linked to the sequence required for expression in the host cell, but is not limited thereto.

Further, the term "operably linked" refers to a functional linkage between a gene sequence and a promoter sequence which initiates and mediates transcription of the polynucleotide encoding the desired polypeptide of the present disclosure.

The term "microorganism including the variant polypeptide" or "microorganism including the variant of 5'-inosinic acid dehydrogenase", as used herein, means a microorganism prepared by providing abilities to produce IMP for a microorganism having a naturally weak abilities to produce IMP or a parent strain having no abilities to produce IMP. Specifically, the microorganism may be a microorganism expressing the variant of 5'-inosinic acid dehydrogenase having the polypeptide including substitution of one or more amino acids in the amino acid sequence of SEQ ID NO: 2, wherein the amino acid substitution may include at least any one selected from the group consisting of substitution of the amino acid at position 377 with threonine and substitution of the amino acid at position 499 from the N-terminus with isoleucine. Firth r, the microorgsaism may be a microorganism expressing the variant polypeptide, wherein the microorganism has 5'-inosinic acid dehydrogenase activity by substitution of the amino acid at position 377 with another amino acid, substitution of the amino acid at position 499 with another amino acid, or substitution of the amino acid at position 377 with another amino acid and substitution of the amino acid at position 499 with another amino acid in the amino acid sequence of SEQ ID NO: 2, but is not limited thereto.

The microorganism may be a cell or a microorganism which may include the polynucleotide encoding the variant of 5'-inosinic acid dehydrogenase, or may be transformed with the vector including the polynucleotide encoding the variant of 5'-inosinic acid dehydrogenase to express the variant of 5'-inosinic acid dehydrogenase, and with respect to the objects of the present disclosure, the host cell or the microorganism may be any microorganism, as long as it includes the variant of 5'-inosinic acid dehydrogenase to produce 5'-inosinic acid.

In the present disclosure, the microorganism producing 5'-inosinic acid may be used interchangeably with a 5'-inosinic acid-producing microorganism or a microorganism having 5'-inosinic acid productivity.

As used herein, the term "microorganism producing 5'-inosinic acid" may be a microorganism where a genetic modification occurs or activity is enhanced in order to produce the desired 5'-inosinic acid, including all of a wild-type microorganism or a microorganism where a genetic modification naturally or artificially occurs, and the microorganism may be a microorganism where a particular mechanism is weakened or enhanced by insertion of an exogenous gene or by enhancement or inactivation of activity of an endogenous gene. With respect to the objects of the present disclosure, the microorganism producing 5'-inosinic acid may be characterized in that the microorganism includes the variant or 5'-inosinic acid dehydrogenase to have increased productivity of desired 5'-inosinic acid, and specifically, the microorganism may be a microorganism of the genus Corynebacterium. Specifically, in the present disclosure, the microorganism producing 5'-inosinic acid or the microorganism having 5'-inosinic acid productivity may be a microorganism where a portion of the genes involved in the 5'-inosinic acid biosynthesis pathway is enhanced or weakened, or a portion of the genes involved in the 5'-inosinic acid degradation pathway is enhanced or weakened. For example, the microorganism may be a microorganism where expression of purF encoding phosphoribosyipyrophosphate amidotransferase is enhanced or expression of purA encoding adenylosuccinate synthetase is weakened, but is not limited thereto.

As used herein, the term "the genus Corynebacterium microorganism producing 5'-inosinic acid" refers to a microorganism of the genus Corynebacterium which has 5'-inosinic acid productivity naturally or by mutation. Specifically, as used herein, the genus Corynebacterium microorganism having 5'-inosinic acid productivity may be a microorganism of the genus Corynebacterium which has improved 5'-inosinic acid productivity by enhancing or weakening activity of the guaB gene encoding 5'-inosinic acid dehydrogenase. More specifically, as used herein, the genus Corynebacterium microorganism having 5'-inosinic acid productivity may be a microorganism of the genus Corynebacterium which has improved 5'-inosinic acid productivity by including the variant of 5'-inosinic acid dehydrogenase or the polynucleotide encoding the same, or by being transformed with the vector including the polynucleotide encoding the variant of 5'-inosinic acid dehydrogenase. The 'microorganism of the genus Corynebacterium which has improved 5'-inosinic acid productivity' means a microorganism having improved 5'-inosinic acid productivity, as compared with a parent strain before transformation or a non-modified microorganism. The 'non-modified microorganism' means a wild-type strain itself, or a microorganism that does not include the variant protein producing 5'-inosinic acid, or a microorganism that is not transformed with the vector including the polynucleotide encoding the variant of 5'-inosinic acid dehydrogenase.

As used herein, the "microorganism of the genus Corynebacterium" may be specifically Corynebacterium glutamicum, Corynebacterium ammoniagenes, Brevibacterium lactofermentum, Brevibacterium flavum, Corynebacterium thermoaminogenes, Corynebacterium efficiens, Corynebacterium stationis, etc., but is not limited thereto.

Still another aspect of the present disclosure provides a method of preparing 5'-inosinic acid, which includes culturing the genus Corynebacterium microorganism producing 5'-inosinic acid in a medium; and recovering 5'-inosinic acid from the microorganism or the medium.

In the method, the step of culturing the microorganism may be performed by a known batch culture, continuous culture, fed-batch culture, etc., but is not particularly limited thereto. In this regard, the culture conditions are not particularly limited, but an optimal pH (e.g., pH 5 to pH 9, specifically pH 6 to pH 8, and most specifically pH 6.8) may be adjusted by using a basic compound (e.g., sodium hydroxide, potassium hydroxide, or ammonia) or an acidic compound (e.g., phosphoric acid or sulfuric acid). An aerobic condition may be maintained by adding oxygen or an oxygen-containing gas mixture to the culture. The culture temperature may be maintained at 20° C. to 45° C., and specifically at 25° C. to 40° C., and the culturing may be performed for about 10 hours to about 160 hours, but is not limited thereto. 5'-Inosinic acid produced by the culturing may be secreted into the medium or may remain within the cells.

Moreover, in a culture medium to be used, as a carbon source, sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), organic acids (e.g., acetic acid), etc. may be used individually or in a mixture, but the carbon source is not limited thereto. As a nitrogen source, a nitrogen-containing organic compound (e.g., peptone, yeast extract, meat extract, malt extract, corn steep liquor, soybean flour, and urea) or an inorganic compound (e.g., ammonium sulfate, ammonium chloride, ammonium phosphate, ammonium carbonate and ammonium nitrate), etc. may be used individually or in a mixture, but the nitrogen source is not limited thereto. As a phosphorus source, potassium dihydrogen phosphate, dipotassium hydrogen phosphate, a sodium-containing salt corresponding thereto, etc. may be used individually or in a mixture, but the phosphorus source is not limited thereto. The medium may also include essential growth-promoting materials such as other metal salts (e.g., magnesium sulfate or iron sulfate), amino acids, and vitamins.

A method of recovering 5'-inosinic acid produced in the culturing step of the present disclosure is to collect 5'-inosinic acid from the culture liquid by using an appropriate method known in the art according to the culturing method. For example, centrifugation, filtration, anion exchange chromatography, crystallization, HPLC, etc. may be used, and the desired 5'-inosinic acid may be recovered from the medium or microorganism by using an appropriate method known in the art.

Further, the recovering step may include a purification process. The purification process may be performed by using an appropriate method known in the art. Therefore, the recovered 5'-inosinic acid may be a purified form or a microorganism fermentation liquid including 5'-inosinic acid (Introduction to Biotechnology and Genetic Engineering, A. J. Nair., 2008).

Hereinafter, the present invention will be described in more detail with reference to Examples. However, it is apparent to those skilled in the art to which the present disclosure pertains that these Examples are for illustrative purposes only, and the scope of the present disclosure invention is not intended to be limited by these Examples.

Example 1: Preparation of Wild Type-Based IMP-Producing

Strain

The wild-type strain of the genus Corynebacterium cannot produce IMP or can produce IMP in a very small amount. Therefore, an IMP-producing strain was prepared based on Corynebacterium stationis ATCC68372. More specifically, the IMP-producing strain was prepared by enhancing activity of PurF encoding phosphoribosylpyrophosphate amidotransferase, which is the first enzyme of the purine biosynthesis, and weakening activity of PurA encoding adenylosuccinate synthetase in the 5'-inosinic acid degradation pathway.

Example 1-1: Preparation of purF-Enhanced Strain

In order to prepare a strain in which the start codon of purF was changed, an insertion vector containing purF was first prepared. In order to clone purF gene into the insertion vector, specifically, PCR was performed using the genomic DNA of Corynebacterium stationis ATCC6872 as a template and primers of SEQ ID NOS: 9 and 10 and SEQ ID NOS: 11 and 12 for 30 cycles of denaturation at 94° C. for 30 sec, annealing at 55° C. for 30 sec, and extension at 72° C. for 2 min. PCR was performed using two DNA fragments obtained by the above PCR as a template and primers of SEQ ID NOS: 9 and 12 for 30 cycles of denaturation at 94° C. for 30 sec, annealing at 55° C. for 30 sec, and extension at 72° C. for 2 min to obtain a DNA fragment. The obtained DNA fragment was cleaved by restriction enzyme XbaI, and cloned into a vector (pDZ (Korean Patent No. 10-0924065 and international Patent Publication No. 2008-033001)) that had been cleaved by the same enzyme. The vector prepared by the above method was designated as pDZ-purF-gla.

TABLE 1

| SEQ ID NO. | Primer | Sequence (5'-3') |
|---|---|---|
| 9 | pDZ-purF(gla)-1 | GCTCTAGACCACTCTAAGACGCGGCCACC |
| 10 | pDZ-purF(gla)-2 | AAGTAGTGTTCACCATGACGCTGATTCTACTAAGTTT |
| 11 | pDZ-purF(gla)-3 | AGTAGAATCAGCGTCATGGTGAACACTACTTTCCCCAG |
| 12 | pDZ-purF(gla)-4 | GCTCTAGACTGTGCGCCCACGATATCCAG |

The recombinant vector pDZ-purF-gla was transformed into Corynebacterium stationis ATCC6872 by electroporation, and then strains in which the vector was inserted into the genomic DNA by homologous recombination were selected on a medium containing 25 mg/L kanamycin. The primary strains thus selected were subjected to secondary crossover, and then selected strains were subjected to sequencing, thereby selecting a desired strain into which the mutation was introduced, and this strain was designated as ATCC68'72::purF(gla) strain.

Example 1-2: Preparation of purA-Weakened Strain

In order to prepare a strain in which the start codon of purA was changed, an insertion vector containing purA was first prepared. In order to clone purA gene into the insertion vector, specifically, PCR was performed using the genomic DNA of Corynebacterium stationis ATCC68.72 as a template and primers of SEQ ID NOS: 13 and 14 and SEQ ID NOS: 15 and 16. Cloning of the PCR products was performed as in Example 1-1, and a vector thus prepared was designated as pDZ-purA-alt.

TABLE 2

| SEQ ID NO. | Primer | Sequence (5'-3') |
|---|---|---|
| 13 | pDZ-purA(alt)-1 | GCTCTAGAGGCCACGATGCCCGGAGCATC |
| 14 | pDZ-purA(alt)-2 | TAACGATAGCTGCCAAGGTTATTCACTTCCTAGATTT |
| 15 | pDZ-purA(alt)-3 | AGGAAGTGAATAACCTTGGCAGCTATCGTTATCGTCG |
| 16 | pDZ-purA(alt)-4 | GCTCTAGAGGGTCACGAATGGGTAGGTGCC |

The recombinant vector pDZ-purA-alt was transformed into ATCC68'2::purF(gla) strain prepared in Example 1-1 by electroporation, and then strains in which the vector was inserted into the genomic DNA by homologous recombination were selected on a medium containing 25 mg/L kanamycin. The primary strains thus selected were subjected to secondary crossover, and then selected strains were subjected to sequencing, thereby selecting a desired strain into which the mutation was introduced.

The finally selected IMP-producing strain based on the wild-type *Corynebacterium stationis* ATCC6872 was designated as CJI2331.

Example 1-3: Fermentation Titer Test of CJI2331

2 mL of a seed culture medium was dispensed into test tubes with a diameter of 18 mm and autoclaved under pressure. Each of ATCC872 and CJI2331 was inoculated and incubated at 30° C. for 24 h with shaking to be used as seed cultures. 29 mL of a fermentation medium was dispensed into 250 mL shaking Erlenmeyer flasks, and autoclaved under pressure at 121° C. for 15 min, and 2 mL of the seed culture was inoculated and incubated for 3 days. Culture conditions were adjusted at a rotation speed of 170 rpm, a temperature of 30° C., and pH 7.5.

After completion of the culturing, amount of IMP produced was measured by HPLC (SHIMAZDU LC2A), and the culturing results are as in Table 3 below. The following results suggest that the purF-enhanced and purA-weakened strain has IMP productivity.

TABLE 3

| Name of strain | IMP (g/L) |
|---|---|
| ATCC6872 | 0 |
| CJI2331 | 1.05 |

Seed culture medium: 11 glucose, 1% peptone, 1 meat extract, 1% yeast extract, 0.25% sodium chloride, 100 mg/L adenine, 100 mg/L guanine, pH 7.5

Fermentation medium: 0.1 sodium glutamate, 1% ammonium chloride, 1.2% magnesium sulfate, 0.01% calcium chloride, 20 mg/L iron sulfate, 20 mg/L manganese sulfate, 20 mg/L zinc sulfate, 5 mg/L copper sulfate, 23 mg/L L-cysteine, 24 mg/L alanine, 0 mg/L nicotinic acid, 45 μg/L biotin, 5 mg/L thiamine hydrochloride, 30 mg/L adenine, 1.9% phosphoric acid (859), 2.559 glucose, 1.45% fructose Example 2: Preparation of 5'-Inosinic Acid Dehydrogenase-Weakened Variant In order to identify a 5'-inosinic acid dehydrogenase mutation which improves IMP productivity, a mutant library of guaB, which is a gene encoding 5'-inosinic acid dehydrogenase, was prepared.

Example 2-1: Preparation of guaB-Containing Vector

In order to prepare a guaB mutant library, a guaB-containing recombinant vector was first prepared. PCR was performed using the genomic DNA of *Corynebacterium stationis* ATCC6872 as a template and primers of SEQ ID NO: 17 and SEQ ID NO: 18, and a PCR product was cloned into *E. coli* vector pCR2.1 by using a TOPO Cloning Kit (Invitrogen) to obtain pCR-guaB.

TABLE 4

| SEQ ID NO. | Primer | Sequence (5'-3') |
|---|---|---|
| 17 | pCR-guaB-F | ACTGCATTACACGGATATGTA |
| 18 | pCR-guaB-R | CCTCGTGGCGTCCCCACAAAC |

Example 2-2: Preparation of guaB Mutant Library

A guaB mutant library was prepared based on the vector prepared in Example 2-1. The library was prepared by using an error-prone PCR kit (clontech Diversify® PCR Random Mutagenesis Kit). Under conditions where mutations may occur, PCR was performed using primers of SEQ ID NO: 19 and SEQ ID NO: 20. Specifically, under conditions where 0 to 3 mutations per 1000 bp may occur, pre-heating was performed at 94° C. for 30 sec, followed by 25 cycles of 94° C. for 30 sec and 68° C. for 1 min 30 sec. A PCR product thus obtained was subjected to PCR using a megaprimer (500 rig to 125 ng) for 2 cycles of 95° C. for 50 sec, 60° C. for 50 sec, and 68° C. for 12 min, and then treated with DpnI, and transformed into *E. coli*) DH5α and spread on an LB solid medium containing kanamycin (25 mg/L) 0.20 kinds of transformed colonies were selected and then plasmids were obtained, followed by sequencing analysis. As a result, it was confirmed that mutations were introduced at different sites at a frequency of 2 mutations/kb. About 20,000 transformed *E. coli* colonies were taken and plasmids were extracted, and designated as a pTOPO-guaB-library.

TABLE 5

| SEQ ID NO. | Primer | Sequence (5'-3') |
|---|---|---|
| 19 | pTOPO-guaB-library-F | ATTGCATGGCTTGACGTTTGA |
| 20 | pTOPT-guaB-library-R | ATCAATGTGCCACTGCGTGCT |

Example 2-3: Evaluation of Prepared Library and Selection of Strain

The pTOPO-guaB-library prepared in Example 2-2 was transformed into the CJI2331 strain prepared in Example 1 by electroporation, and then spread on a nutrient medium containing 25 mg/L kanamycin to obtain 10,000 colonies into which the mutant gene was inserted. Each of the colonies was designated as CJI2331_pTOPO_guaB(mt)1 to CJI2331_pTOPO_guaB (mt)1000.

Nutrient medium: 1% peptone, 1% meat extract, 0.25% sodium chloride, 1% yeast extract, 21 agar, pH 7.2

Each of the obtained 10,000 colonies was inoculated in 200 μL of a seed culture medium autoclaved under pressure, and cultured in a 96-deep well plate with shaking at 30° C., 1200 rpm for 24 h by using a microplate shaker (TAITEC), and then used as a seed culture. 290 μL of fermentation medium autoclaved under pressure was dispensed into a 96-deep well plate, and 20 μL of each of the seed cultures was inoculated thereto, followed by culturing with shaking under the same conditions as above for 72 h.

In order to analyze production of 5'-inosinic acid in the culture medium, after completion of the culturing, 3 μL of culture supernatant was transferred to a 96-well UV-plate, each well containing 197 μL of distilled water. Next, a microplate reader was used to perform shaking for 30 sec, and a spectrophotometer was used to measure optical density at 25° C., 270 nm, and compared with optical density of the CJI2331 strain to select 50 mutant strain colonies showing 10% or more increase in the optical density. Other colonies showed similar or decreased optical density, as compared with the regulatory.

Optical densities of the 50 selected strains were measured in the same manner as above to repeatedly examine production amounts of 5'-inosinic acid. Three strains of CJI2331_pTOPO_guaB (mt)133, CJI2331_pTOPO_guaB (mt) 1209, and CJI2331_pTOPO_guaB(mt)3927, which showed remarkable improvement in 5'-inosinic acid productivity, as compared with the CJI2331 strain, were selected.

Example 2-4: Identification of Mutation by Sequencing

In order to identify gene mutations of the mutant strains, each of CJI2331_pTOPO_guaB(mt)133, CJI2331_pTOPO_guaB(m01209, and CJI2331_pTOPO_guaB(mt)8927 was subjected to PCR using primers of SEQ ID NOS: 21 and 27, followed by sequencing. Their guaB genes were compared with those of the wild-type strain ATCC6872 and CJI2331.

As a result, all of the three strains were found to include guaB gene mutation at different sites.

Specifically, it was confirmed that the CJI2331 pTOPO_guaB(mt)133 strain has a substitution mutation of threonine at position 499 to isoleucine, the CJI2331_pTOPO_guaB(mt)1209 strain has a substitution mutation of alanine at position 377 to threonine, and the CJI2331_pTOPO_guaB(mt) 927 strain has a substitution mutation of alanine at position 377 to threonine and a substitution mutation of threonine at position 499 to isoleucine in the amino acid sequence of GuaB gene represented by SEQ ID NO: 2. Therefore, in the following Examples 3 and 4, it was examined whether each of the above mutations affected amount of IMP produced of the microorganism of the genus *Corynebacterium*.

Example 3: Examination of IMP Productivity in CJI2331

The mutations identified in Example 2 were introduced into CJI2331, which is an ATCC6872-derived IMP-producing strain, and IMP productivity was examined.

Example 3-1: Preparation of Mutation-Introduced Strain

In order to introduce the mutations identified in Example 2, reverse oligonucleotides containing the target mutations were designed in a length of 75-mer, respectively.

Specifically, 30 μg of an oligonucleotide of SEQ ID NO: 23 or 24 was transformed into the CJI2331 strain by an electric pulse method (Appl. Microbiol. Biothcenol., 1999, 52:541-545), and 1 mL of a complex liquid medium was added thereto, followed by culturing with shaking at 30° C. and 160 rpm for 30 min. Thereafter, the culture was incubated in ice for 10 min-, and centrifuged at 4° C. and 4000 rpm for 10 min, and the supernatant was discarded to obtain a cell pellet. Then, 1 mL or a 10 glycerol solution at 4° was added thereto, followed by mixing. The mixture was centrifuged at 4° C. and 4000 rpm for 10 min. The supernatant was discarded and a cell pellet was washed. The cell pellet was washed once again, and 0.1 mL of 1.0% glycerol solution at 4° C. was added thereto to prepare cells for subsequent transformation. Thereafter, the cells were transformed with the oligonucleotide of SEQ ID NO: 23 or 24 by the above electric pulse method, and this procedure was repeated ten times. The cells were spread on a complex agar plate to obtain colonies (Nat. Protcc., 2014 October; 9 (10):2301-16).

Sequencing analysis of the obtained colonies was performed. As a result, the target mutations were found to be introduced into the strains. The strain introduced with A377T mutation in the protein encoded by guaB gene was designated as CJI2331_guaB_m1, and the strain introduced with T499I mutation in the same protein was designated as CJI2331_guaB_m2.

Further, in order to prepare a mutant strain including both of A377T and T499I mutations, 30 μg of the oligonucleotide of SEQ ID NO: 24 was transformed into CJI2331_guaB_m1 strain, and colonies were obtained in the same manner as above (Nat. Protoc., 2014 October; 9(10):2301-16). Sequencing analysis of the obtained colonies was performed, and a strain introduced with both of A377T and T499I mutations in the protein encoded by guaB gene was selected and designated as CJI2331_guaB_m1m2.

TABLE 6

| SEQ ID NO. | Primer | Sequence (5'-3') |
|---|---|---|
| 23 | mage A377T | ACAATCACGATGTCACCAGGAGCCTCCAGGGTG CCTGTGAACATCGAGCCCAGCATGACCGAGTCC GCGCCAGCA |
| 24 | mage T499I | TATTTTTAATCCTTAACGGTAGTTCGGAGCTTC TACAATTTGCTGCAGGTGGTGCGGGTGCGACTC AGCCAAGCC |

Example 3-2: Examination of IMP Productivity in Mutation-Introduced Strains 2 mL of a seed culture medium was dispensed into test tubes with a diameter of 18 mm and autoclaved under pressure. Each of ATCC6872 and CJI2331 was inoculated and incubated at 30° C. for 24 h with shaking to be used as seed cultures. 29 mL of a fermentation medium was dispensed into 250 mL shaking Erlenmeyer flasks, and autoclaved under pressure at 121° C. for 15 min, and 2 mL of the seed culture was inoculated and incubated for 3 days. Culture conditions were adjusted at a rotation speed of 170 rpm, a temperature of 30° C., and PH 7.5.

After completion of the culturing, the amount of IMP produced was measured by HPLC (SHIMAZDU LC20A), and the results are as in the following Table 7. As shown in the following results, the CJI2331_guaB_m1 or CJI2331_guaB_m2 strain having A377T mutation or T499I mutation in the protein encoded by guaB gene showed IMP concentration improvement of 0.42 q/L (40%) or 0.21 q/L (20%), respectively, as compared with the regulatory CJI2331 strain. Further, the CJI2331_guaB_m1m2 strain having both of A377T and T499I mutations snowed the most improvement IMP concentration of 0.58 g/L (50), suggesting that the most effective improvement in IMP concentration may be obtained when both of the two mutations are included.

TABLE 7

| Strain | IMP (g/L) |
| --- | --- |
| CJI2331 | 1.05 |
| CJI2331_guaB_m1 | 1.47 |
| CJI2331_guaB_m2 | 1.26 |
| CJI2331_guaB_m1m2 | 1.58 |

Example 4: Examination of IMP Productivity in IMP-Producing Strain Derived from ATCC6872

Example 4-1: Selection of IMP-Producing Strain Derived from ATCC6872

In order to prepare an IMP-producing strain derived from ATCC6872, ATCC672 was suspended in a phosphate buffer (pH 7.0) or a citrate buffer (pH 5.5) at a density of 10 cells/mL to $10^8$ cells/ML, and then treated with UV at room temperature or 32° C. for 20 min to 40 min to induce mutations. The strain was washed with a 0.85% saline solution twice, and spread on a minimal medium containing 1.7% agar which was supplemented with a substance for providing a resistance at a proper concentration, and thus colonies were obtained. Each colony was cultured in a nutrient medium, and cultured in a seed culture medium for 24 h, and then cultured in a fermentation medium for 3 to 4 days. As a result, a colony was selected which showed the most excellent production of IMP which had accumulated in the culture medium. To prepare a strain producing a high concentration of IMP, adenine-auxotroph, guanine-leaky type, lysozyme sensitivity, 3,4-dehydroproline resistance, streptomycin resistance, azetidine carboxylic acid resistance, thiaproline resistance, azaserine resistance, sulfaguanidine resistance, norvaline resistance, and trimethoprim resistance were provided by the above procedure, sequentially. CJI2335 provided with the above resistances and having excellent IMP productivity was finally selected. Resistance of CJI2335 relative to ATCC6872 was compared and shown in the following Table 8.

TABLE 8

| Characteristic | ATCC6872 | CJI2335 |
| --- | --- | --- |
| Adenine-auxotroph | Non-auxotroph | Auxotroph |
| Guanine-leaky type | Non-auxotroph | Leaky type |
| Lysozyme sensitivity | 80 µg/mL | 8 µg/mL |
| 3,4-Dehydroproline resistance | 1000 µg/mL | 3500 µg/mL |
| Streptomycin resistance | 500 µg/mL | 2000 µg/mL |
| Azetidine carboxylic acid resistance | 5 mg/mL | 30 mg/mL |
| Thiaproline resistance | 10 µg/mL | 100 µg/mL |
| Azaserine resistance | 25 µg/mL | 100 µg/mL |
| Sulfaguanidine resistance | 50 µg/mL | 200 µg/mL |
| Norvaline resistance | 0.2 mg/mL | 2 mg/mL |
| Trimethoprim resistance | 20 µg/mL | 100 µg/mL |

Minimal medium: 2% glucose, 0.3% sodium sulfate, 0.11 potassium phosphate monobasic, 0.3% potassium phosphate dibasic, 0.3% magnesium sulfate, 10 mg/L calcium chloride, 10 mg/L iron sulfate, 1 mg/b zinc sulfate, 3.6 mg/L manganese chloride, 20 mg/b L-cysteine, 10 mg/L calcium pantothenate, 5 mg/L thiamine hydrochloride, 30 µg/L biotin, 20 mg/L adenine, 20 mg/L guanine, adjusted to pH 7.3.

Example 4-2: Fermentation Titer Test of CJI2335

2 mL of a seed culture medium was dispensed into test tubes with a diameter of 18 min and autoclaved under pressure. Each of ATCC68'12 and CJI2335 was inoculated and incubated at 30° C. for 24 h with shaking to be used as seed cultures. 29 µL of a fermentation medium was dispensed into 250 mL shaking Erlenmeyer flasks, and autoclaved under pressure at 121° C. for 15 min, and 2 mL of the seed culture was inoculated and incubated for 3 days. Culture conditions were adjusted at a rotation speed of 170 rpm, a temperature of 30° C., and PH 7.5

After completion of the culturing, the amount IMP produced was measured by HPLC (SHIMAZDU LC20A), and the results are as in the following Table 9.

TABLE 9

| Strain | IMP (g/L) |
| --- | --- |
| ATCC6872 | 0 |
| CJI2335 | 5.4 |

Example 4-3: Preparation of Insertion Vector Containing guaB Mutation

In order to introduce strains with the mutation selected in Example 3, an insertion vector was prepared. A vector for introduction of guaB mutation was prepared as follows. PCR was performed using the guaB(A377T) gene of the CJI2331_pTOPO_guaB(mt)209 strain and the guaB(T499I) gene of the CJI2331_pTOPO_guaB(mt)133 strain selected in Example 2 as a template and primers of SEQ ID NO: 25 and SEQ ID NO: 26. PCR was performed by denaturation at 94° C. for 5 min, and then, for 20 cycles of at 94° C. for 30 sec, at 55° C. for 30 sec, at 72° C. for 1 min, followed by polymerization at 72° C. for 5 min. The resulting gene fragments were each cleaved by XbaI. Each of the gene fragments which had been cleaved by restriction enzyme XbaI was cloned into a linear pDZ vector by using T4 ligase, and thus pDZ-guaB(A377T) and pDZ-guaB(T499I) were prepared.

TABLE 10

| SEQ ID NO. | Primer | Sequence (5'-3') |
| --- | --- | --- |
| 25 | pDZ-guaB-F | GCTCTAGAGACATGACTATCCAGGAAGTT |
| 26 | pDZ-guaB-R | GCTCTAGAATCAATGTGCCACTGCGTGCT |

Example 4-4: Introduction of Mutant into CJI2335 Strain and Evaluation

In order to confirm the nucleotide sequence of the guaB gene of the CJI2335 strain selected in Example 4-1, genomic DNA of CJI2335 was amplified by PCR. Specifically, PCR was first performed using chromosomal DNA of CJI2335 as a template and primers of SEQ ID NOS: 21 and 2-2-27 for 28 cycles of polymerization at 94° C. for 1 min, at 58° C. for 30 sec, and at 72° C. for 2 min with Taq DNA polymerase to amplify guaB of about 2.1 kb. Sequencing thereof was performed using the same primers, and as a result, its sequence was the same as that of guaB gene of the wild-type ATCC6872, indicating no mutation in guaB gene.

TABLE 11

| SEQ. ID NO. | Primer | Sequence (5'-3') |
|---|---|---|
| 21 | guaB-seq-F | AATGAAAGATGCCGGATCATT |
| 27 | guaB-seq-R | TCAATGTGCCACTGCGTGCT |

TABLE 12

| Strain | IMP (g/L) |
|---|---|
| CJI2335 | 5.4 |
| CJI2335_guaB_m1 | 7.6 |
| CJI2335_guaB_m2 | 6.4 |
| CJI2335_guaB_m1m2 | 8.1 |

CJI2335 was transformed with each of pDZ-guaB (A377T) and pDZ-guaB(T499I) vectors prepared in Example 4-3, and strains in which the vector was inserted into the genomic DNA by homologous recombination were selected on a medium containing 25 mg/L kanamycin. The primary strains thus selected were subjected to secondary crossover to select strains into which the target gene mutation was introduced. Introduction of the gene mutation into the desired transformed strains was examined by PCR using primers of SEQ ID NO: 21 and SEQ ID NO: 2227, and then sequencing was performed to confirm introduction of the mutation into the strains. Specifically, the strain introduced with A377T mutation in the protein encoded by guaB gene was designated as CJI2335_guaB_m1, and the strain introduced with T499I mutation in the protein encoded by guaB gene was designated as CJI2335_guaB_m2. Further, in order to prepare a mutant strain having both of A377T and T499I mutations, CJI2335_guaB_m1 strain was transformed with the pDZ-guaB(T499I) vector, and colonies were obtained in the same manner as above. For sequencing analysis of the obtained colonies, a strain introduced with both of A377I and T499I mutations in the protein encoded by guaB gene was selected and designated as CJI2335_guaB_m1m2.

As shown in Table 12, the CJI2335_guaB_m1 or CJI2335_guaB_m2 strain having A377T mutation or T499I T mutation in the protein encoded by guaB gene showed IMP concentration of 2.2 g/L (402) or 1.0 g/L (18.52), respectively, indicating improvement, as compared with the regulatory CJI2335 strain. Further, the CJI2331_guaB_m1m2 strain having both of A377T and T499I mutations showed IMP concentration improvement of 2.7 g/L (5%), indicating that when both of the two mutations are included, most effective improvement may be obtained in IMP concentration.

These results support that when the variant of 5'-inosinic acid dehydrogenase of the present disclosure is introduced into various kinds of the genus Corynebacterium microorganism having IMP productivity, 5'-inosinic acid productivity may be greatly improved.

CJI2335 was deposited at the Korean Culture Center of Microorganisms on Jun. 22, 2018, under the provisions of the Budapest Treaty and assigned accession number KCCM112278P. Further, the prepared CJI2335_guaB_m1m2 strain, also called CJI2347, was deposited at the Korean Culture Center of Microorganisms on Jun. 22, 2018, under the provisions of the Budapest Treaty and assigned accession number KCCM12279P.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the present disclosure is defined by the appended claims rather than by the description preceding them, and therefore all changes and modifications that fall within metes and bounds of the claims, or equivalents of such metes and bounds are therefore intended to be embraced by the claims.

Name of depository institution: Korean Collection for Type Cultures (foreign)
Deposit Accession Number: KCCM12278P
Deposit date: 20100622
Name of depository institution: Korean Collection for Type Cultures (foreign)
Deposit Accession Number: KCCM12279P
Deposit date: 20180622

Effect of the Invention

When the genus Corynebacterium microorganism producing 5'-inosinic acid is cultured using a variant of 5'-inosinic acid dehydrogenase of the present disclosure, it is possible to produce 5'-inosinic acid in a high yield.

The invention claimed is:

1. A variant of 5'-inosinic acid dehydrogenase comprising the amino acid sequence of SEQ ID NO:2 and having i) substitution of the amino acid at position 377 with threonine, ii) substitution of the amino acid at position 499 with isoleucine, or iii) substitution of the amino acid at position 377 with threonine and substitution of the amino acid at position 499 with isoleucine.

2. A polynucleotide encoding the variant of 5'-inosinic acid dehydrogenase of claim 1.

3. A vector comprising the polynucleotide of claim 2.

4. A 5'-inosinic acid producing microorganism of the genus *Corynebacterium*, wherein the microorganism comprises the variant of 5'-inosinic acid dehydrogenase of claim 1.

5. The 5'-inosinic acid producing microorganism of the genus *Corynebacterium* of claim 4, wherein the microorganism is *Corynebacterium stationis*.

6. A method of preparing 5'-inosinic acid, comprising: culturing the microorganism of claim 4 in a medium; and recovering 5'-inosinic acid from the microorganism or the medium.

7. The method of preparing 5'-inosinic acid of claim 6, wherein the microorganism is *Corynebacterium stationis*.

8. A 5'-inosinic acid producing microorganism of the genus *Corynebacterium*, wherein the microorganism comprises the vector of claim 3.

9. The 5'-inosinic acid producing microorganism of the genus *Corynebacterium* of claim 8, wherein the microorganism is *Corynebacterium stationis*.

10. A method of preparing 5'-inosinic acid, comprising: culturing the microorganism of claim 8 in a medium; and recovering 5'-inosinic acid from the microorganism or the medium.

11. The method of preparing 5'-inosinic acid of claim 10, wherein the microorganism is *Corynebacterium stationis*.

12. A 5'-inosinic acid producing microorganism of the genus *Corynebacterium*, wherein the microorganism comprises the polynucleotide of claim 2.

13. The microorganism of claim 12, wherein the microorganism is *Corynebacterium stationis*.

14. A method of preparing 5'-inosinic acid, comprising: culturing the microorganism of claim 12 in a medium; and recovering 5'-inosinic acid from the microorganism or the medium.

15. The method of preparing 5'-inosinic acid of claim 14, wherein the microorganism is *Corynebacterium stationis*.

* * * * *

UNITED STATES PATENT AND TRADEMARK OFFICE
CERTIFICATE OF CORRECTION

| | | |
|---|---|---|
| PATENT NO. | : 11,066,687 B2 | Page 1 of 1 |
| APPLICATION NO. | : 16/482608 | |
| DATED | : July 20, 2021 | |
| INVENTOR(S) | : Ji Hye Lee et al. | |

It is certified that error appears in the above-identified patent and that said Letters Patent is hereby corrected as shown below:

On the Title Page

Item (30), insert:
--(30) Foreign Application Priority Data
Jul. 27, 2018 (KR) ...............10-2018-0087597--

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 27

<210> SEQ ID NO 1
<211> LENGTH: 1521
<212> TYPE: DNA
<213> ORGANISM: Unknown
<220> FEATURE:
<223> OTHER INFORMATION: guaB NT

<400> SEQUENCE: 1

```
atgaccgaaa atcgtgtttc taccggtgga gatgacccaa ataaggttgc attgcatggc      60
ttgacgtttg atgacgtgct gctgctacct gccgaatcca atgttgttcc gtcggaagta     120
gacacttcgg cgcagttcac ccgcaatact cgtttaggta ttcctttggc atcggctgcg     180
atggacacgg ttactgaggc gcgcatggct attgccatgg cacgccaggg tggcattggt     240
gtcttgcacc gcaacttgtc ctcgcaagag caggcggagc aggtcgaaat cgtcaagcgc     300
```

```
tctgagtccg gcatggtcac cgaccctgtg accgcgaatc cagacatgac tatccaggaa    360
gttgatgacc tgtgtgcacg cttccgcatc tctggtcttc ctgtggtcaa cgaagacggc    420
accttgttgg gcatttgcac caaccgcgat atgcgctttg agcgcgacta ttcccgcaag    480
gtttctgaca tcatgaccgc tatgccgctg gttgtggcaa agaaggcgt cagcaaggaa     540 gaagccctgg atctgctgtc gacgaacaag gtagaaaagc tacctatcgt tgataaaaac    600
aacaagctgt tcggtctgat taccgttaaa gactttgtta agaccgaaca gttcccgaat    660
tcctccaagg atgcttcggg ccgcttgcta gtagcagcag gtattggtac cggcgaggag    720
tcttatgagc gtgcaggctt gcttgtcgat gccggcgtgg acgttctcat tgtcgactcc    780
gcacacgcgc acaataaccg cgtgctggaa atggtctcgc gcgtcaagaa tgacttcggc    840
tccaagattg atgttgtcgg cggcaacctg gcaacacgct cggcagcaaa ggcgatgatt    900
gaggctggcg cagacgccat caaggtgggt attggtcctg gttctatctg caccacccgt    960
gtggttgctg tgttggtgc accacagatt accgcgatca tggaagcagc taccgtggct    1020
tctgctgcgg gcgtgccttt gattgcagac ggcggcatgc agtactccgg tgacgttgct    1080
aaggctttgg ctgctggcgc ggactcggtc atgctgggct cgatgttcgc aggcaccctg    1140
gaggctcctg gtgacatcgt gattgtcggc ggcaagcagt acaagcgcta ccgcggcatg    1200
ggttcgatgg cgctatgca aggccgtggc ctctccggcg agaagcgttc ttactccaag    1260
gaccgctact tccaggcaga tgtgcgcagc gaagataagc tggttccaga aggcgtggaa    1320
ggcaaggttc cttaccgcgg cgaaattggt cagattaccc accagattgt gggcggtttg    1380
cgcgcggcaa tgggctacac tggctccgct actattgaag agctgaagac caagcagttc    1440
gtgcgtatta ccactgctgg cttggctgag tcgcacccgc accacctgca gcaaactgta    1500
gaagctccga actaccgtta a                                              1521
```

<210> SEQ ID NO 2
<211> LENGTH: 506
<212> TYPE: PRT
<213> ORGANISM: Unknown
<220> FEATURE:
<223> OTHER INFORMATION: guaB AA

<400> SEQUENCE: 2

```
Met Thr Glu Asn Arg Val Ser Thr Gly Gly Asp Asp Pro Asn Lys Val
1               5                   10                  15

Ala Leu His Gly Leu Thr Phe Asp Asp Val Leu Leu Pro Ala Glu
            20                  25                  30

Ser Asn Val Val Pro Ser Glu Val Asp Thr Ser Ala Gln Phe Thr Arg
        35                  40                  45

Asn Thr Arg Leu Gly Ile Pro Leu Ala Ser Ala Ala Met Asp Thr Val
    50                  55                  60

Thr Glu Ala Arg Met Ala Ile Ala Met Ala Arg Gln Gly Gly Ile Gly
65                  70                  75                  80

Val Leu His Arg Asn Leu Ser Ser Gln Glu Gln Ala Glu Gln Val Glu
                85                  90                  95

Ile Val Lys Arg Ser Glu Ser Gly Met Val Thr Asp Pro Val Thr Ala
            100                 105                 110

Asn Pro Asp Met Thr Ile Gln Glu Val Asp Asp Leu Cys Ala Arg Phe
        115                 120                 125

Arg Ile Ser Gly Leu Pro Val Val Asn Glu Asp Gly Thr Leu Leu Gly
    130                 135                 140
```

Ile Cys Thr Asn Arg Asp Met Arg Phe Glu Arg Asp Tyr Ser Arg Lys
145                 150                 155                 160

Val Ser Asp Ile Met Thr Ala Met Pro Leu Val Val Ala Lys Glu Gly
                165                 170                 175

Val Ser Lys Glu Glu Ala Leu Asp Leu Leu Ser Thr Asn Lys Val Glu
            180                 185                 190

Lys Leu Pro Ile Val Asp Lys Asn Asn Lys Leu Val Gly Leu Ile Thr
        195                 200                 205

Val Lys Asp Phe Val Lys Thr Glu Gln Phe Pro Asn Ser Ser Lys Asp
    210                 215                 220

Ala Ser Gly Arg Leu Leu Val Ala Ala Gly Ile Gly Thr Gly Glu Glu
225                 230                 235                 240

Ser Tyr Glu Arg Ala Gly Leu Leu Val Asp Ala Gly Val Asp Val Leu
                245                 250                 255

Ile Val Asp Ser Ala His Ala His Asn Asn Arg Val Leu Glu Met Val
            260                 265                 270

Ser Arg Val Lys Asn Asp Phe Gly Ser Lys Ile Asp Val Val Gly Gly
        275                 280                 285

Asn Leu Ala Thr Arg Ser Ala Ala Lys Ala Met Ile Glu Ala Gly Ala
    290                 295                 300

Asp Ala Ile Lys Val Gly Ile Gly Pro Gly Ser Ile Cys Thr Thr Arg
305                 310                 315                 320

Val Val Ala Gly Val Gly Ala Pro Gln Ile Thr Ala Ile Met Glu Ala
                325                 330                 335

Ala Thr Val Ala Ser Ala Ala Gly Val Pro Leu Ile Ala Asp Gly Gly
            340                 345                 350

Met Gln Tyr Ser Gly Asp Val Ala Lys Ala Leu Ala Ala Gly Ala Asp
        355                 360                 365

Ser Val Met Leu Gly Ser Met Phe Ala Gly Thr Leu Glu Ala Pro Gly
    370                 375                 380

Asp Ile Val Ile Val Gly Gly Lys Gln Tyr Lys Arg Tyr Arg Gly Met
385                 390                 395                 400

Gly Ser Met Gly Ala Met Gln Gly Arg Gly Leu Ser Gly Glu Lys Arg
                405                 410                 415

Ser Tyr Ser Lys Asp Arg Tyr Phe Gln Ala Asp Val Arg Ser Glu Asp
            420                 425                 430

Lys Leu Val Pro Glu Gly Val Glu Gly Lys Val Pro Tyr Arg Gly Glu
        435                 440                 445

Ile Gly Gln Ile Thr His Gln Ile Val Gly Gly Leu Arg Ala Ala Met
    450                 455                 460

Gly Tyr Thr Gly Ser Ala Thr Ile Glu Glu Leu Lys Thr Lys Gln Phe
465                 470                 475                 480

Val Arg Ile Thr Thr Ala Gly Leu Ala Glu Ser His Pro His Leu
                485                 490                 495

Gln Gln Thr Val Glu Ala Pro Asn Tyr Arg
            500                 505

<210> SEQ ID NO 3
<211> LENGTH: 1521
<212> TYPE: DNA
<213> ORGANISM: Unknown
<220> FEATURE:
<223> OTHER INFORMATION: guaB NT(A377T)

<400> SEQUENCE: 3

-continued

| | |
|---|---|
| atgaccgaaa atcgtgtttc taccggtgga gatgacccaa ataaggttgc attgcatggc | 60 |
| ttgacgtttg atgacgtgct gctgctacct gccgaatcca atgttgttcc gtcggaagta | 120 |
| gacacttcgg cgcagttcac ccgcaatact cgtttaggta ttcctttggc atcggctgcg | 180 |
| atggacacgg ttactgaggc gcgcatggct attgccatgg cacgccaggg tggcattggt | 240 |
| gtcttgcacc gcaacttgtc ctcgcaagag caggcggagc aggtcgaaat cgtcaagcgc | 300 |
| tctgagtccg gcatggtcac cgaccctgtg accgcgaatc cagacatgac tatccaggaa | 360 |
| gttgatgacc tgtgtgcacg cttccgcatc tctggtcttc ctgtggtcaa cgaagacggc | 420 |
| accttgttgg gcatttgcac caaccgcgat atgcgctttg agcgcgacta ttcccgcaag | 480 |
| gtttctgaca tcatgaccgc tatgccgctg ttgtggcaa agaaggcgt cagcaaggaa | 540 |
| gaagccctgg atctgctgtc gacgaacaag gtagaaaagc tacctatcgt tgataaaaac | 600 |
| aacaagctgg tcggtctgat taccgttaaa gactttgtta agaccgaaca gttcccgaat | 660 |
| tcctccaagg atgcttcggg ccgcttgcta gtagcagcag gtattggtac cggcgaggag | 720 |
| tcttatgagc gtgcaggctt gcttgtcgat gccggcgtgg acgttctcat tgtcgactcc | 780 |
| gcacacgcgc acaataaccg cgtgctggaa atggtctcgc gcgtcaagaa tgacttcggc | 840 |
| tccaagattg atgttgtcgg cggcaacctg gcaacacgct cggcagcaaa ggcgatgatt | 900 |
| gaggctggcg cagacgccat caaggtgggt attggtcctg gttctatctg caccacccgt | 960 |
| gtggttgctg gtgttggtgc accacagatt accgcgatca tggaagcagc taccgtggct | 1020 |
| tctgctgcgg gcgtgccttt gattgcagac ggcggcatgc agtactccgg tgacgttgct | 1080 |
| aaggctttgg ctgctggcgc ggactcggtc atgctgggct cgatgttcac aggcaccctg | 1140 |
| gaggctcctg gtgacatcgt gattgtcggc ggcaagcagt acaagcgcta ccgcggcatg | 1200 |
| ggttcgatgg gcgctatgca aggccgtggc ctctccggcg agaagcgttc ttactccaag | 1260 |
| gaccgctact tccaggcaga gtgcgcagcg aagataagc tggttccaga aggcgtggaa | 1320 |
| ggcaaggttc cttaccgcgg cgaaattggt cagattaccc accagattgt gggcggtttg | 1380 |
| cgcgcggcaa tgggctacac tggctccgct actattgaag agctgaagac caagcagttc | 1440 |
| gtgcgtatta ccactgctgg cttggctgag tcgcacccgc accacctgca gcaaactgta | 1500 |
| gaagctccga actaccgtta a | 1521 |

<210> SEQ ID NO 4
<211> LENGTH: 1521
<212> TYPE: DNA
<213> ORGANISM: Unknown
<220> FEATURE:
<223> OTHER INFORMATION: guaB NT(T499I)

<400> SEQUENCE: 4

| | |
|---|---|
| atgaccgaaa atcgtgtttc taccggtgga gatgacccaa ataaggttgc attgcatggc | 60 |
| ttgacgtttg atgacgtgct gctgctacct gccgaatcca atgttgttcc gtcggaagta | 120 |
| gacacttcgg cgcagttcac ccgcaatact cgtttaggta ttcctttggc atcggctgcg | 180 |
| atggacacgg ttactgaggc gcgcatggct attgccatgg cacgccaggg tggcattggt | 240 |
| gtcttgcacc gcaacttgtc ctcgcaagag caggcggagc aggtcgaaat cgtcaagcgc | 300 |
| tctgagtccg gcatggtcac cgaccctgtg accgcgaatc cagacatgac tatccaggaa | 360 |
| gttgatgacc tgtgtgcacg cttccgcatc tctggtcttc ctgtggtcaa cgaagacggc | 420 |
| accttgttgg gcatttgcac caaccgcgat atgcgctttg agcgcgacta ttcccgcaag | 480 |

| | |
|---|---|
| gtttctgaca tcatgaccgc tatgccgctg gttgtggcaa agaaggcgt cagcaaggaa | 540 |
| gaagccctgg atctgctgtc gacgaacaag gtagaaaagc tacctatcgt tgataaaaac | 600 |
| aacaagctgg tcggtctgat taccgttaaa gactttgtta agaccgaaca gttcccgaat | 660 |
| tcctccaagg atgcttcggg ccgcttgcta gtagcagcag gtattggtac cggcgaggag | 720 |
| tcttatgagc gtgcaggctt gcttgtcgat gccggcgtgg acgttctcat tgtcgactcc | 780 |
| gcacacgcgc acaataaccg cgtgctggaa atggtctcgc gcgtcaagaa tgacttcggc | 840 |
| tccaagattg atgttgtcgg cggcaacctg gcaacacgct cggcagcaaa ggcgatgatt | 900 |
| gaggctggcg cagacgccat caaggtgggt attggtcctg gttctatctg caccacccgt | 960 |
| gtggttgctg gtgttggtgc accacagatt accgcgatca tggaagcagc taccgtggct | 1020 |
| tctgctgcgg gcgtgccttt gattgcagac ggcggcatgc agtactccgg tgacgttgct | 1080 |
| aaggctttgg ctgctggcgc ggactcggtc atgctgggct cgatgttcgc aggcaccctg | 1140 |
| gaggctcctg gtgacatcgt gattgtcggc ggcaagcagt acaagcgcta ccgcggcatg | 1200 |
| ggttcgatgg gcgctatgca aggccgtggc ctctccggcg agaagcgttc ttactccaag | 1260 |
| gaccgctact tccaggcaga gtgcgcagc gaagataagc tggttccaga aggcgtggaa | 1320 |
| ggcaaggttc cttaccgcgg cgaaattggt cagattaccc accagattgt gggcggtttg | 1380 |
| cgcgcggcaa tgggctacac tggctccgct actattgaag agctgaagac caagcagttc | 1440 |
| gtgcgtatta ccactgctgg cttggctgag tcgcacccgc accacctgca gcaaattgta | 1500 |
| gaagctccga actaccgtta a | 1521 |

<210> SEQ ID NO 5
<211> LENGTH: 1521
<212> TYPE: DNA
<213> ORGANISM: Unknown
<220> FEATURE:
<223> OTHER INFORMATION: guaB NT(A377T, T499I)

<400> SEQUENCE: 5

| | |
|---|---|
| atgaccgaaa atcgtgtttc taccggtgga gatgacccaa ataaggttgc attgcatggc | 60 |
| ttgacgtttg atgacgtgct gctgctacct gccgaatcca atgttgttcc gtcggaagta | 120 |
| gacacttcgg cgcagttcac ccgcaatact cgtttaggta ttccttggc atcggctgcg | 180 |
| atggacacgg ttactgaggc gcgcatggct attgccatgg cacgccaggg tggcattggt | 240 |
| gtcttgcacc gcaacttgtc ctcgcaagag caggcggagc aggtcgaaat cgtcaagcgc | 300 |
| tctgagtccg gcatggtcac cgaccctgtg accgcgaatc cagacatgac tatccaggaa | 360 |
| gttgatgacc tgtgtgcacg cttccgcatc tctggtcttc ctgtggtcaa cgaagacggc | 420 |
| accttgttgg gcatttgcac caaccgcgat atgcgctttg agcgcgacta ttcccgcaag | 480 |
| gtttctgaca tcatgaccgc tatgccgctg gttgtggcaa agaaggcgt cagcaaggaa | 540 |
| gaagccctgg atctgctgtc gacgaacaag gtagaaaagc tacctatcgt tgataaaaac | 600 |
| aacaagctgg tcggtctgat taccgttaaa gactttgtta agaccgaaca gttcccgaat | 660 |
| tcctccaagg atgcttcggg ccgcttgcta gtagcagcag gtattggtac cggcgaggag | 720 |
| tcttatgagc gtgcaggctt gcttgtcgat gccggcgtgg acgttctcat tgtcgactcc | 780 |
| gcacacgcgc acaataaccg cgtgctggaa atggtctcgc gcgtcaagaa tgacttcggc | 840 |
| tccaagattg atgttgtcgg cggcaacctg gcaacacgct cggcagcaaa ggcgatgatt | 900 |
| gaggctggcg cagacgccat caaggtgggt attggtcctg gttctatctg caccacccgt | 960 |
| gtggttgctg gtgttggtgc accacagatt accgcgatca tggaagcagc taccgtggct | 1020 |

```
tctgctgcgg gcgtgccttt gattgcagac ggcggcatgc agtactccgg tgacgttgct    1080
aaggctttgg ctgctggcgc ggactcggtc atgctgggct cgatgttcac aggcaccctg    1140
gaggctcctg gtgacatcgt gattgtcggc ggcaagcagt acaagcgcta ccgcggcatg    1200
ggttcgatgg cgctatgca aggccgtggc ctctccggcg agaagcgttc ttactccaag    1260
gaccgctact tccaggcaga tgtgcgcagc gaagataagc tggttccaga aggcgtggaa    1320
ggcaaggttc cttaccgcgg cgaaattggt cagattaccc accagattgt gggcggtttg    1380
cgcgcggcaa tgggctacac tggctccgct actattgaag agctgaagac caagcagttc    1440
gtgcgtatta ccactgctgg cttggctgag tcgcacccgc accacctgca gcaaattgta    1500
gaagctccga actaccgtta a                                              1521
```

<210> SEQ ID NO 6
<211> LENGTH: 506
<212> TYPE: PRT
<213> ORGANISM: Unknown
<220> FEATURE:
<223> OTHER INFORMATION: GuaB(A377T)-AA

<400> SEQUENCE: 6

```
Met Thr Glu Asn Arg Val Ser Thr Gly Gly Asp Asp Pro Asn Lys Val
1               5                   10                  15

Ala Leu His Gly Leu Thr Phe Asp Asp Val Leu Leu Leu Pro Ala Glu
            20                  25                  30

Ser Asn Val Val Pro Ser Glu Val Asp Thr Ser Ala Gln Phe Thr Arg
        35                  40                  45

Asn Thr Arg Leu Gly Ile Pro Leu Ala Ser Ala Ala Met Asp Thr Val
    50                  55                  60

Thr Glu Ala Arg Met Ala Ile Ala Met Ala Arg Gln Gly Gly Ile Gly
65                  70                  75                  80

Val Leu His Arg Asn Leu Ser Ser Gln Glu Gln Ala Glu Gln Val Glu
                85                  90                  95

Ile Val Lys Arg Ser Glu Ser Gly Met Val Thr Asp Pro Val Thr Ala
            100                 105                 110

Asn Pro Asp Met Thr Ile Gln Glu Val Asp Asp Leu Cys Ala Arg Phe
        115                 120                 125

Arg Ile Ser Gly Leu Pro Val Val Asn Glu Asp Gly Thr Leu Leu Gly
    130                 135                 140

Ile Cys Thr Asn Arg Asp Met Arg Phe Glu Arg Asp Tyr Ser Arg Lys
145                 150                 155                 160

Val Ser Asp Ile Met Thr Ala Met Pro Leu Val Val Ala Lys Glu Gly
                165                 170                 175

Val Ser Lys Glu Glu Ala Leu Asp Leu Leu Ser Thr Asn Lys Val Glu
            180                 185                 190

Lys Leu Pro Ile Val Asp Lys Asn Asn Lys Leu Val Gly Leu Ile Thr
        195                 200                 205

Val Lys Asp Phe Val Lys Thr Glu Gln Phe Pro Asn Ser Ser Lys Asp
    210                 215                 220

Ala Ser Gly Arg Leu Leu Val Ala Ala Gly Ile Gly Thr Gly Glu Glu
225                 230                 235                 240

Ser Tyr Glu Arg Ala Gly Leu Leu Val Asp Ala Gly Val Asp Val Leu
                245                 250                 255

Ile Val Asp Ser Ala His Ala His Asn Asn Arg Val Leu Glu Met Val
            260                 265                 270
```

```
Ser Arg Val Lys Asn Asp Phe Gly Ser Lys Ile Asp Val Gly Gly
        275                 280                 285

Asn Leu Ala Thr Arg Ser Ala Lys Ala Met Ile Glu Ala Gly Ala
        290                 295                 300

Asp Ala Ile Lys Val Gly Ile Gly Pro Gly Ser Ile Cys Thr Thr Arg
305                 310                 315                 320

Val Val Ala Gly Val Gly Ala Pro Gln Ile Thr Ala Ile Met Glu Ala
                325                 330                 335

Ala Thr Val Ala Ser Ala Gly Val Pro Leu Ile Ala Asp Gly Gly
        340                 345                 350

Met Gln Tyr Ser Gly Asp Val Ala Lys Ala Leu Ala Ala Gly Ala Asp
        355                 360                 365

Ser Val Met Leu Gly Ser Met Phe Thr Gly Thr Leu Glu Ala Pro Gly
        370                 375                 380

Asp Ile Val Ile Val Gly Gly Lys Gln Tyr Lys Arg Tyr Arg Gly Met
385                 390                 395                 400

Gly Ser Met Gly Ala Met Gln Gly Arg Gly Leu Ser Gly Glu Lys Arg
                405                 410                 415

Ser Tyr Ser Lys Asp Arg Tyr Phe Gln Ala Asp Val Arg Ser Glu Asp
        420                 425                 430

Lys Leu Val Pro Glu Gly Val Glu Gly Lys Val Pro Tyr Arg Gly Glu
        435                 440                 445

Ile Gly Gln Ile Thr His Gln Ile Val Gly Gly Leu Arg Ala Ala Met
        450                 455                 460

Gly Tyr Thr Gly Ser Ala Thr Ile Glu Glu Leu Lys Thr Lys Gln Phe
465                 470                 475                 480

Val Arg Ile Thr Thr Ala Gly Leu Ala Glu Ser His Pro His His Leu
                485                 490                 495

Gln Gln Thr Val Glu Ala Pro Asn Tyr Arg
        500                 505

<210> SEQ ID NO 7
<211> LENGTH: 506
<212> TYPE: PRT
<213> ORGANISM: Unknown
<220> FEATURE:
<223> OTHER INFORMATION: GuaB(T499I)-AA

<400> SEQUENCE: 7

Met Thr Glu Asn Arg Val Ser Thr Gly Gly Asp Asp Pro Asn Lys Val
1               5                   10                  15

Ala Leu His Gly Leu Thr Phe Asp Asp Val Leu Leu Leu Pro Ala Glu
                20                  25                  30

Ser Asn Val Val Pro Ser Glu Val Asp Thr Ser Ala Gln Phe Thr Arg
        35                  40                  45

Asn Thr Arg Leu Gly Ile Pro Leu Ala Ser Ala Ala Met Asp Thr Val
        50                  55                  60

Thr Glu Ala Arg Met Ala Ile Ala Met Ala Arg Gln Gly Gly Ile Gly
65                  70                  75                  80

Val Leu His Arg Asn Leu Ser Ser Gln Glu Gln Ala Glu Gln Val Glu
                85                  90                  95

Ile Val Lys Arg Ser Glu Ser Gly Met Val Thr Asp Pro Val Thr Ala
                100                 105                 110

Asn Pro Asp Met Thr Ile Gln Glu Val Asp Asp Leu Cys Ala Arg Phe
        115                 120                 125
```

Arg Ile Ser Gly Leu Pro Val Asn Glu Asp Gly Thr Leu Leu Gly
130                 135                 140

Ile Cys Thr Asn Arg Asp Met Arg Phe Glu Arg Asp Tyr Ser Arg Lys
145                 150                 155                 160

Val Ser Asp Ile Met Thr Ala Met Pro Leu Val Val Ala Lys Glu Gly
                165                 170                 175

Val Ser Lys Glu Glu Ala Leu Asp Leu Leu Ser Thr Asn Lys Val Glu
            180                 185                 190

Lys Leu Pro Ile Val Asp Lys Asn Asn Lys Leu Val Gly Leu Ile Thr
        195                 200                 205

Val Lys Asp Phe Val Lys Thr Glu Gln Phe Pro Asn Ser Ser Lys Asp
210                 215                 220

Ala Ser Gly Arg Leu Leu Val Ala Ala Gly Ile Gly Thr Gly Glu Glu
225                 230                 235                 240

Ser Tyr Glu Arg Ala Gly Leu Leu Val Asp Ala Gly Val Asp Val Leu
                245                 250                 255

Ile Val Asp Ser Ala His Ala His Asn Asn Arg Val Leu Glu Met Val
            260                 265                 270

Ser Arg Val Lys Asn Asp Phe Gly Ser Lys Ile Asp Val Val Gly Gly
        275                 280                 285

Asn Leu Ala Thr Arg Ser Ala Ala Lys Ala Met Ile Glu Ala Gly Ala
290                 295                 300

Asp Ala Ile Lys Val Gly Ile Gly Pro Gly Ser Ile Cys Thr Thr Arg
305                 310                 315                 320

Val Val Ala Gly Val Gly Ala Pro Gln Ile Thr Ala Ile Met Glu Ala
                325                 330                 335

Ala Thr Val Ala Ser Ala Gly Val Pro Leu Ile Ala Asp Gly Gly
            340                 345                 350

Met Gln Tyr Ser Gly Asp Val Ala Lys Ala Leu Ala Ala Gly Ala Asp
        355                 360                 365

Ser Val Met Leu Gly Ser Met Phe Ala Gly Thr Leu Glu Ala Pro Gly
370                 375                 380

Asp Ile Val Ile Val Gly Gly Lys Gln Tyr Lys Arg Tyr Arg Gly Met
385                 390                 395                 400

Gly Ser Met Gly Ala Met Gln Gly Arg Gly Leu Ser Gly Glu Lys Arg
                405                 410                 415

Ser Tyr Ser Lys Asp Arg Tyr Phe Gln Ala Asp Val Arg Ser Glu Asp
            420                 425                 430

Lys Leu Val Pro Glu Gly Val Glu Gly Lys Val Pro Tyr Arg Gly Glu
        435                 440                 445

Ile Gly Gln Ile Thr His Gln Ile Val Gly Gly Leu Arg Ala Ala Met
450                 455                 460

Gly Tyr Thr Gly Ser Ala Thr Ile Glu Glu Leu Lys Thr Lys Gln Phe
465                 470                 475                 480

Val Arg Ile Thr Thr Ala Gly Leu Ala Glu Ser His Pro His Leu
                485                 490                 495

Gln Gln Ile Val Glu Ala Pro Asn Tyr Arg
        500                 505

<210> SEQ ID NO 8
<211> LENGTH: 506
<212> TYPE: PRT
<213> ORGANISM: Artificial Sequence
<220> FEATURE:

<223> OTHER INFORMATION: GuaB(A377T,T499I)-AA

<400> SEQUENCE: 8

```
Met Thr Glu Asn Arg Val Ser Thr Gly Gly Asp Asp Pro Asn Lys Val
1               5                   10                  15

Ala Leu His Gly Leu Thr Phe Asp Asp Val Leu Leu Leu Pro Ala Glu
            20                  25                  30

Ser Asn Val Val Pro Ser Glu Val Asp Thr Ser Ala Gln Phe Thr Arg
        35                  40                  45

Asn Thr Arg Leu Gly Ile Pro Leu Ala Ser Ala Ala Met Asp Thr Val
    50                  55                  60

Thr Glu Ala Arg Met Ala Ile Ala Met Ala Arg Gln Gly Gly Ile Gly
65                  70                  75                  80

Val Leu His Arg Asn Leu Ser Ser Gln Glu Gln Ala Glu Gln Val Glu
                85                  90                  95

Ile Val Lys Arg Ser Glu Ser Gly Met Val Thr Asp Pro Val Thr Ala
            100                 105                 110

Asn Pro Asp Met Thr Ile Gln Glu Val Asp Asp Leu Cys Ala Arg Phe
        115                 120                 125

Arg Ile Ser Gly Leu Pro Val Val Asn Glu Asp Gly Thr Leu Leu Gly
    130                 135                 140

Ile Cys Thr Asn Arg Asp Met Arg Phe Glu Arg Asp Tyr Ser Arg Lys
145                 150                 155                 160

Val Ser Asp Ile Met Thr Ala Met Pro Leu Val Val Ala Lys Glu Gly
                165                 170                 175

Val Ser Lys Glu Glu Ala Leu Asp Leu Leu Ser Thr Asn Lys Val Glu
            180                 185                 190

Lys Leu Pro Ile Val Asp Lys Asn Asn Lys Leu Val Gly Leu Ile Thr
        195                 200                 205

Val Lys Asp Phe Val Lys Thr Glu Gln Phe Pro Asn Ser Ser Lys Asp
    210                 215                 220

Ala Ser Gly Arg Leu Leu Val Ala Ala Gly Ile Gly Thr Gly Glu Glu
225                 230                 235                 240

Ser Tyr Glu Arg Ala Gly Leu Leu Val Asp Ala Gly Val Asp Val Leu
                245                 250                 255

Ile Val Asp Ser Ala His Ala His Asn Asn Arg Val Leu Glu Met Val
            260                 265                 270

Ser Arg Val Lys Asn Asp Phe Gly Ser Lys Ile Asp Val Val Gly Gly
        275                 280                 285

Asn Leu Ala Thr Arg Ser Ala Ala Lys Ala Met Ile Glu Ala Gly Ala
    290                 295                 300

Asp Ala Ile Lys Val Gly Ile Gly Pro Gly Ser Ile Cys Thr Thr Arg
305                 310                 315                 320

Val Val Ala Gly Val Gly Ala Pro Gln Ile Thr Ala Ile Met Glu Ala
                325                 330                 335

Ala Thr Val Ala Ser Ala Ala Gly Val Pro Leu Ile Ala Asp Gly Gly
            340                 345                 350

Met Gln Tyr Ser Gly Asp Val Ala Lys Ala Leu Ala Ala Gly Ala Asp
        355                 360                 365

Ser Val Met Leu Gly Ser Met Phe Thr Gly Thr Leu Glu Ala Pro Gly
    370                 375                 380

Asp Ile Val Ile Val Gly Gly Lys Gln Tyr Lys Arg Tyr Arg Gly Met
385                 390                 395                 400
```

```
Gly Ser Met Gly Ala Met Gln Gly Arg Gly Leu Ser Gly Glu Lys Arg
            405                 410                 415

Ser Tyr Ser Lys Asp Arg Tyr Phe Gln Ala Asp Val Arg Ser Glu Asp
        420                 425                 430

Lys Leu Val Pro Glu Gly Val Glu Gly Lys Val Pro Tyr Arg Gly Glu
    435                 440                 445

Ile Gly Gln Ile Thr His Gln Ile Val Gly Gly Leu Arg Ala Ala Met
450                 455                 460

Gly Tyr Thr Gly Ser Ala Thr Ile Glu Glu Leu Lys Thr Lys Gln Phe
465                 470                 475                 480

Val Arg Ile Thr Thr Ala Gly Leu Ala Glu Ser His Pro His His Leu
            485                 490                 495

Gln Gln Ile Val Glu Ala Pro Asn Tyr Arg
        500                 505

<210> SEQ ID NO 9
<211> LENGTH: 29
<212> TYPE: DNA
<213> ORGANISM: Artificial Sequence
<220> FEATURE:
<223> OTHER INFORMATION: primer pDZ-purF(g1a)-1

<400> SEQUENCE: 9
gctctagacc actctaagac gcggccacc                                    29

<210> SEQ ID NO 10
<211> LENGTH: 37
<212> TYPE: DNA
<213> ORGANISM: Artificial Sequence
<220> FEATURE:
<223> OTHER INFORMATION: primer pDZ-purF(g1a)-2

<400> SEQUENCE: 10
aagtagtgtt caccatgacg ctgattctac taagttt                            37

<210> SEQ ID NO 11
<211> LENGTH: 38
<212> TYPE: DNA
<213> ORGANISM: Artificial Sequence
<220> FEATURE:
<223> OTHER INFORMATION: primer pDZ-purF(g1a)-3

<400> SEQUENCE: 11
agtagaatca gcgtcatggt gaacactact ttccccag                           38

<210> SEQ ID NO 12
<211> LENGTH: 29
<212> TYPE: DNA
<213> ORGANISM: Artificial Sequence
<220> FEATURE:
<223> OTHER INFORMATION: primer pDZ-purF(g1a)-4

<400> SEQUENCE: 12
gctctagact gtgcgcccac gatatccag                                    29

<210> SEQ ID NO 13
<211> LENGTH: 29
<212> TYPE: DNA
<213> ORGANISM: Artificial Sequence
<220> FEATURE:
<223> OTHER INFORMATION: primer pDZ-purA(a1t)-1

<400> SEQUENCE: 13
```
gctctagagg ccacgatgcc cggagcatc                                              29

<210> SEQ ID NO 14
<211> LENGTH: 37
<212> TYPE: DNA
<213> ORGANISM: Artificial Sequence
<220> FEATURE:
<223> OTHER INFORMATION: primer pDZ-purA(alt)-2

<400> SEQUENCE: 14
taacgatagc tgccaaggtt attcacttcc tagattt                                     37

<210> SEQ ID NO 15
<211> LENGTH: 37
<212> TYPE: DNA
<213> ORGANISM: Artificial Sequence
<220> FEATURE:
<223> OTHER INFORMATION: primer pDZ-purA(alt)-3

<400> SEQUENCE: 15
aggaagtgaa taaccttggc agctatcgtt atcgtcg                                     37

<210> SEQ ID NO 16
<211> LENGTH: 29
<212> TYPE: DNA
<213> ORGANISM: Artificial Sequence
<220> FEATURE:
<223> OTHER INFORMATION: primer pDZ-purA(alt)-4

<400> SEQUENCE: 16
gctctagagg tcacgaatgg gtaggtgcc                                              29

<210> SEQ ID NO 17
<211> LENGTH: 21
<212> TYPE: DNA
<213> ORGANISM: Artificial Sequence
<220> FEATURE:
<223> OTHER INFORMATION: primer pCR-guaB-F

<400> SEQUENCE: 17
actgcattac acggatatgt a                                                      21

<210> SEQ ID NO 18
<211> LENGTH: 21
<212> TYPE: DNA
<213> ORGANISM: Artificial Sequence
<220> FEATURE:
<223> OTHER INFORMATION: primer pCR-guaB-R

<400> SEQUENCE: 18
cctcgtggcg tccccacaaa c                                                      21

<210> SEQ ID NO 19
<211> LENGTH: 21
<212> TYPE: DNA
<213> ORGANISM: Artificial Sequence
<220> FEATURE:
<223> OTHER INFORMATION: primer pTOPO-guaB-library-F

<400> SEQUENCE: 19
attgcatggc ttgacgtttg a                                                      21

<210> SEQ ID NO 20
<211> LENGTH: 21
<212> TYPE: DNA
<213> ORGANISM: Artificial Sequence

```
<220> FEATURE:
<223> OTHER INFORMATION: primer pTOPT-guaB-library-R

<400> SEQUENCE: 20
atcaatgtgc cactgcgtgc t                                                    21

<210> SEQ ID NO 21
<211> LENGTH: 21
<212> TYPE: DNA
<213> ORGANISM: Artificial Sequence
<220> FEATURE:
<223> OTHER INFORMATION: primer guaB seq F

<400> SEQUENCE: 21
aatgaaagat gccggatcat t                                                    21

<210> SEQ ID NO 22
<211> LENGTH: 21
<212> TYPE: DNA
<213> ORGANISM: Artificial Sequence
<220> FEATURE:
<223> OTHER INFORMATION: primer guaB seq R

<400> SEQUENCE: 22
acgcccgaat cacgaacctg a                                                    21

<210> SEQ ID NO 23
<211> LENGTH: 75
<212> TYPE: DNA
<213> ORGANISM: Artificial Sequence
<220> FEATURE:
<223> OTHER INFORMATION: primer mage A337T

<400> SEQUENCE: 23
acaatcacga tgtcaccagg agcctccagg gtgcctgtga acatcgagcc cagcatgacc          60
gagtccgcgc cagca                                                           75

<210> SEQ ID NO 24
<211> LENGTH: 75
<212> TYPE: DNA
<213> ORGANISM: Artificial Sequence
<220> FEATURE:
<223> OTHER INFORMATION: primer mage T499I

<400> SEQUENCE: 24 tattttaat ccttaacggt agttcggagc ttctacaatt tgctgcaggt ggtgcgggtg           60
cgactcagcc aagcc                                                           75

<210> SEQ ID NO 25
<211> LENGTH: 29
<212> TYPE: DNA
<213> ORGANISM: Artificial Sequence
<220> FEATURE:
<223> OTHER INFORMATION: primer pDZ-guaB-F

<400> SEQUENCE: 25
gctctagaga catgactatc caggaagtt                                            29

<210> SEQ ID NO 26
<211> LENGTH: 29
<212> TYPE: DNA
<213> ORGANISM: Artificial Sequence
<220> FEATURE:
<223> OTHER INFORMATION: primer pDZ-guaB-R
```

```
<400> SEQUENCE: 26
gctctagaca gtggtgtaat ccaccacgc                                          29

<210> SEQ ID NO 27
<211> LENGTH: 20
<212> TYPE: DNA
<213> ORGANISM: Artificial Sequence
<220> FEATURE:
<223> OTHER INFORMATION: primer guaB-seq-R

<400> SEQUENCE: 27
tcaatgtgcc actgcgtgct                                                    20
```